United States Patent [19]

Killman et al.

[11] 4,137,916

[45] Feb. 6, 1979

[54] CATHETER PLUG ASSEMBLY

[75] Inventors: Don M. Killman, Irving; Thomas P. Robinson, Dallas, both of Tex.

[73] Assignee: Travenol Laboratories, Inc., Deerfield, Ill.

[21] Appl. No.: 743,925

[22] Filed: Nov. 22, 1976

[51] Int. Cl.$^2$ .............................................. A61M 5/00
[52] U.S. Cl. ................................... 128/214.4; 128/221
[58] Field of Search ............... 128/214, 214.4, 218 P, 128/218 N, 221

[56] References Cited

U.S. PATENT DOCUMENTS

| 2,575,425 | 11/1951 | Nelson | 128/218 P |
| 2,902,034 | 9/1959 | Simmonds | 128/218 P |
| 3,055,361 | 9/1962 | Ballard | 128/214.4 |
| 3,215,141 | 11/1965 | Podhora | 128/214.4 |
| 3,406,685 | 10/1968 | May | 128/214.4 |
| 3,809,081 | 5/1974 | Loveless | 128/214.4 |

Primary Examiner—Dalton L. Truluck
Attorney, Agent, or Firm—Richards, Harris & Medlock

[57] ABSTRACT

An obturator plug is provided with a thin circumferential deformable sealing skirt integrally formed on and protruding from the plug, engaging the inwardly facing wall of a female catheter fitting to form an improved obturator-catheter assembly having a catheter secured to its proximal end in a female catheter fitting and receiving an obturator having a shaft secured to a plug, the obturator plug including locking means engaging a predetermined portion of the female catheter fitting to lock the plug to the fitting after a specific degree of insertion of the plug into the fitting.

2 Claims, 5 Drawing Figures

CATHETER PLUG ASSEMBLY

This invention relates to catheter plug assemblies, and more particularly to an improved form of plug incorporated in such assemblies as obturators or the like.

In medical infusion procedures, a flexible catheter is often introduced into the vascular system of the patient for prolonged periods of time. The catheter, provided exteriorly of the patient at its proximal end with a female Luer fitting for connection to infusion or pressure monitoring sources, may be only intermittently used for infusion. When not in use, the indwelling catheter frequently is provided with an obturator to occlude the catheter tubing and prevent the build-up of dried blood therein, so that the catheter passage will remain usable.

Such obturators in the prior art typically are provided with a shaft for insertion into the catheter tubing and a plug secured to the proximal end of the shaft for securement in the female catheter fitting. Locking means are provided on the obturator plug for engaging a locking surface on the catheter fittings to secure the obturator in position. For example, the obturator has been provided with a locking dog or ear so that, after insertion of the obturator to the predetermined design depth in a fitting, the obturator may be rotated to lock it to the fitting by engagement of the dog on a flange on the catheter fitting.

The present invention may be used for an improved catheter plug assembly employing such general operating principals. One of the problems which occurs in the prior art devices of this type arise from unavoidable variations in molding production dimensions of particular catheter fittings and obturators. Such variations may result in a significant number of obturators which do not fully effectively seal, and even significant numbers which are not usable with a catheter fitting being employed on a patient. If the obturator plug is too long or wide relative to the inner dimension of the catheter fitting, it may not be possible to insert the obturator plug sufficiently into the fitting to permit the obturator locking dog to engage the locking flange on the catheter, resulting in an unusable combination which will require the obturator to be discarded. On the other hand, if the obturator is too narrow or short relative to the inner dimensions of the catheter fitting, an effective seal may not be achieved. Such unplanned production variations in dimensions may occur in either the fitting or the obturator plug, and even though they may be minor in an absolute dimensional sense, they may result in the problems discussed above.

An object of this invention is to provide an improved plug for such an obturator-catheter assembly which will significantly improve the performance of such assemblies by reducing the potential problems created by production variation in molded dimensions of the elements of the assembly.

The present invention is usable in the environment of an obturator having a shaft secured to a plug, the plug including locking means for engaging a predetermined portion of a female catheter fitting to lock the plug in the fitting at a predetermined degree of insertion of the plug into the fittings. This invention contemplates the provision of a thin circumferential deformable sealing skirt integrally formed on and protruding from the distal end of the plug for engaging the inwardly facing wall of the catheter fitting. A resilient deformable sealing skirt improves the sealing characteristics of such plugs, particularly where dimensional variations are encountered. Moreover, the resilient skirt may be deformed by axial movement of the obturator plug into the fitting where it is necessary to advance the plug into the catheter for engagement with the locking means provided thereon.

In a particular aspect, the plug is provided with a sealing skirt which flares outwardly from the body of the obturator plug at an angle of approximately 20 degrees to the axis of the obturator shaft.

For a more complete understanding of the present invention and for further objects and advantages thereof, reference may now be had to the following description taken in conjunction with the accompanying drawings, in which.

Figure 1:
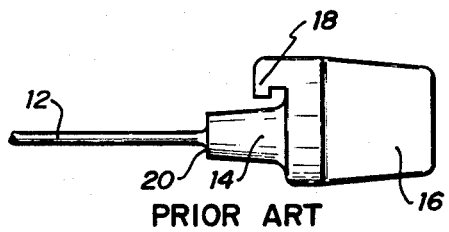
FIG. 1 is a plan view of an obturator characteristic of the prior art.

As illustrated in FIG. 1, prior art obturators have been utilized in the past which employ an obturator plug locking arrangement for cooperation with a flanged female catheter fitting. Such a prior art obturator may be characterized by an elongate slender flexible shaft 12 connected at its proximal end to a plug 14. Plug 14 is provided with a handle 16 for gripping the obturator and inserting it into a catheter, and is also provided with a locking dog 18 for engagement with a female catheter fitting. The obturator is used in conjunction with indwelling catheters for occluding the passage when the catheter is not in use. The obturator is used by inserting the shaft 12 through the female catheter fitting into the catheter, engaging obturator plug 14 sealingly with the interior of the female catheter fitting and locking it into position by turning the obturator to an angle of about 90 degrees to engage locking dog 18 on a flange formed on the catheter fitting. The plug portion 14 of such prior art obturators is typically formed with a relatively smooth distal end 20. The plug 14 has a substantially cylindrical configuration, although typically there might be a very gradual tapering down of the plug 14 in the distal direction.

If the relative fit of the obturator plug 14 and its intended site for use, the female catheter fitting, varies dimensionally from that of design, as through production molding variations or any other reason, then problems may be created. If the obturator plug 14 is relatively too large or long for the female fitting, whether by inadvertent variation in the fitting or in the obturator plug, it may not be possible to insert the plug 14 sufficiently that locking dog 18 may be engaged upon the catheter fitting flange. On the other hand if the relative variation occurs in the other direction where the obturator plug 14 is slightly narrower or shorter with respect to the fitting and design, protective seals may not be produced.

Figure 2:
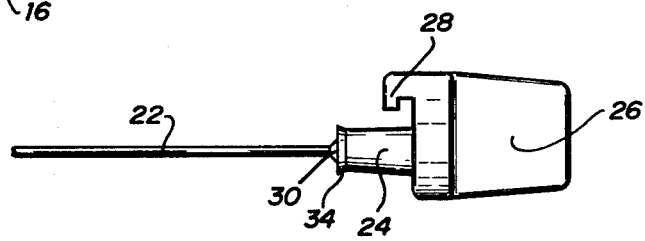
FIG. 2 is a plan view of an obturator constructed in accordance with the present invention.
Figure 3:
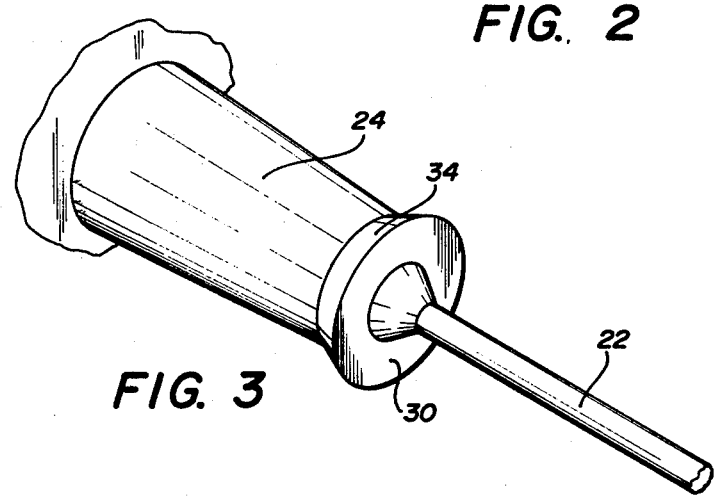
FIG. 3 is a perspective view of the plug portion of the obturator illustrated in FIG. 2.
Figure 4:
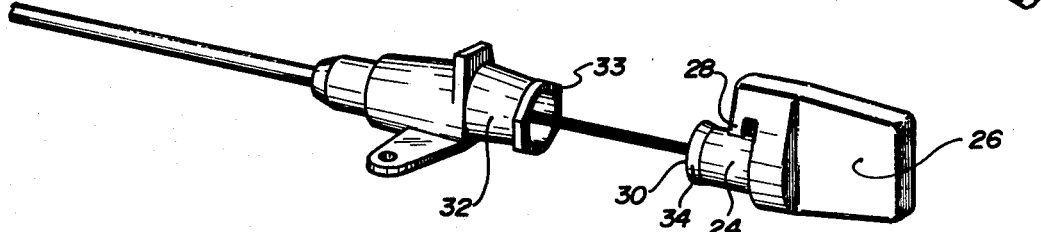
FIG. 4 is a perspective view showing the intermediate stage of insertion of the obturator of FIGS. 2 and 3 into a female catheter fitting.
Figure 5:
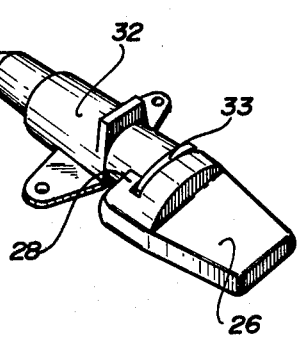
FIG. 5 is a perspective view showing such an obturator inserted into a catheter fitting and locked thereto.

The improved obturator of this invention, as illustrated in FIGS. 2 and 3, is provided with a plug having a thin, circumferential deformable sealing skirt integrally formed on and protruding from the plug for engaging the inwardly facing wall of a female catheter fitting. The improved obturator has an elongate resilient shaft 22, a plug 24, handle 26 and locking dog 28. The distal end of the plug 24 is provided with a protruding resilient sealing skirt 30 circumferentially surrounding and protruding from the distal end of plug 24. The obturator including sealing skirt 30 may be integrally molded from material such as nylon. In the embodiment illustrated, the sealing skirt 30 is provided by a sharply outwardly flared surface 34 at the distal end of plug 24. In one example of the obturator so illustrated, the angle of flare is about 20 degrees, and the diameter of the plug 24 increases over the range of the skirt from 0.155 inches to 0.165 inches. The skirt 30 is sufficiently thin and resilient so that it may be deformed if necessary to permit insertion of the plug 24 to enable locking dog 28 to engage the catheter fitting 32. The step of inserting the obturator into a catheter fitting 32 is illustrated in FIG. 4, with the final locked position of the obturator in catheter fitting 32 illustrated in FIG. 5. In FIG. 5, the obturator plug 24 is fully inserted and turned to engage the locking dog 28 on the flange 33 of catheter fitting 32.

Although preferred embodiments of the invention have been illustrated in the accompanying drawings and described in the foregoing detailed description, it will be understood that the invention is not limited to the embodiments disclosed, but is capable of numerous rearrangements, modifications, and substitution of parts and elements without departing from the spirit and scope of the invention.

What is claimed is:

1. In an obturator comprising a forwardly tapered male plug with a shaft extending from the forward end thereof, said plug including locking means for releasable engagement with projecting dogs on a catheter fitting having an inwardly tapered smooth female portion upon insertion of the obturator into the catheter fitting, the improvement comprising:
   a relatively thin resilient sealing skirt integrally formed about the circumference of the plug substantially flush with the forward end thereof, said sealing skirt tapering radially outwardly at an acute angle to the longitudinal axis of said shaft to provide sealing engagement with the inside circumference of the female portion of said catheter fitting despite minor dimensional variations in manufacturing said plug and catheter fitting which could otherwise prevent suitable sealing engagement when the locking means of the male plug is engaged with the projecting dogs of the catheter fitting.

2. The improvement of claim 1 wherein said sealing skirt diverges radially outwardly from the remaining portion of said plug at an angle of approximately 20 degrees to the longitudinal axis of said obturator shaft.

* * * * *